(12) United States Patent
Razack (10) Patent No.: US 10,849,510 B1
(45) Date of Patent: Dec. 1, 2020

(54) METHODS OF ARTERIAL PRESSURE MONITORING

(71) Applicant: Razack Intellectual Properties, LLC, St. Petersburg, FL (US)

(72) Inventor: Nasser Razack, St. Petersburg, FL (US)

(73) Assignee: Razack Intellectual Properties, LLC, St. Petersburg, FL (US)

( * ) Notice: Subject to any disclaimer, the term of this patent is extended or adjusted under 35 U.S.C. 154(b) by 0 days.

(21) Appl. No.: 16/902,248

(22) Filed: Jun. 15, 2020

Related U.S. Application Data (60) Provisional application No. 62/942,653, filed on Dec. 2, 2019.

(51) Int. Cl.
*A61B 5/0215* (2006.01)
*A61B 5/00* (2006.01)
*A61M 25/09* (2006.01)
*A61M 25/01* (2006.01)

(52) U.S. Cl.
CPC .......... *A61B 5/0215* (2013.01); *A61B 5/6852* (2013.01); *A61B 2505/05* (2013.01); *A61M 25/0169* (2013.01); *A61M 25/09* (2013.01)

(58) Field of Classification Search
CPC .... A61B 5/0215–02158; A61B 5/6852; A61B 2505/05; A61M 25/0169; A61M 25/09
USPC ........................................................ 600/486
See application file for complete search history.

(56) References Cited

U.S. PATENT DOCUMENTS

| | | | | |
|---|---|---|---|---|
| 5,046,497 A | * | 9/1991 | Millar | A61B 5/14539 600/309 |
| 5,295,969 A | * | 3/1994 | Fischell | A61M 25/0693 604/168.01 |
| 7,625,353 B2 | * | 12/2009 | Grandt | A61M 25/0021 604/103.04 |
| 10,470,797 B1 | * | 11/2019 | Rai | A61M 25/06 |
| 2020/0214627 A1 | * | 7/2020 | Christian | A61B 5/0452 |

OTHER PUBLICATIONS

Rundback, John, et al. "Percutaneous stent-graft repair of anastomotic pseudoaneurysms following vascular bypass procedures: a report of two cases." Case Reports in Vascular Medicine 2013 (2013) (Year: 2013).*

Moore WS, Ahn SS, editors: Endovascular surgery, ed 4, Philadelphia, 2011, Saunders, p. 55. (Year: 2011).*

* cited by examiner

*Primary Examiner* — David J. McCrosky
*Assistant Examiner* — Chanel J Jhin
(74) *Attorney, Agent, or Firm* — Shay Glenn LLP (57) ABSTRACT

Methods of monitoring arterial blood using an arterial line tube positions adjacent to a groin sheath, as part of a surgical intervention. Described herein are methods and apparatuses (e.g., systems) for introduction of an arterial line tube for contemporaneous and sensitive blood pressure monitoring along with other instrumentation in the course of a therapeutic intervention through a femoral artery, affording improved monitoring results.

20 Claims, 4 Drawing Sheets

METHODS OF ARTERIAL PRESSURE MONITORING

CLAIM FOR PRIORITY

This patent application claims priority to U.S. Provisional Patent Application No. 62/942,653, filed on Dec. 2, 2019 (titled "METHODS OF ARTERIAL PRESSURE MONITORING"), and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods described herein are directed to introducing and using arterial blood pressure instrumentation for monitoring arterial blood pressure in preparation, during and after invasive diagnostic or therapeutic interventions within the vasculature of a subject.

BACKGROUND

Many diagnostics or therapeutic treatments require access to the vasculature of a subject, and also rely upon hemodynamic monitoring of blood pressure as the diagnostic or therapeutic instrumentation is introduced, used and withdrawn. Performing these functions within the small dimensions of an artery can cause other instrumentation to jar or erratically displace an arterial line used for the hemodynamic monitoring, and may affect the ability to retain the arterial line after the other instrumentation is withdrawn. It is desirable to find new methods of introducing instrumentation along with the arterial line monitoring equipment to isolate and insulate the arterial line equipment from such displacement or jarring, to reduce the artifacts caused by adjacent instrumentation movement. It may also be useful to provide hemodynamic monitoring through a separate (e.g., second) conduit that would be unaltered while devices were being placed in and out of the original arterial sheath. Described herein are methods and apparatuses that may address these needs.

SUMMARY OF THE DISCLOSURE

Described herein are methods and apparatuses (including systems and devices) for hemodynamic monitoring that provide a separate, and in some cases parallel, channel for accessing the arterial vasculature for hemodynamic monitoring. An arterial sheath may be used to pull catheters and devices in and out of the vasculature. The apparatuses (and methods of using them) described herein may provide a separate and isolated conduit running alongside a principle arterial sheath that may be placed in parallel and used for uninterrupted hemodynamic monitoring during a surgical procedure; this apparatus could be left and after the procedure to perform continuous hemodynamic monitoring after the original arterial sheath was removed.

For example, in a first aspect, a method for monitoring an arterial blood pressure is provided, including introducing a first and a second wire into a first sheath (e.g., groin sheath) within a femoral artery and removing the first groin sheath from the femoral artery. In some variations, at this point two wires may be held in place with manual pressure, for example, a first, e.g., 0.018 inch wire for the introduction of the hemodynamic monitoring device may be used and an arterial sheath may be placed over a second wire, such as a 0.035 inch wire. Once the hemodynamic monitoring device is introduced over the 0.018 inch wire and the arterial sheath is introduced over the 0.035 inch wire, both wires can be removed, providing an arterial sheath which can be used to introduce catheters and devices to treat the patient and a hemodynamic monitoring device adjacent to it. The method may therefore include introducing a second groin sheath over the second wire into the femoral artery; introducing an arterial line tube over the first wire into the femoral artery; performing a surgical procedure; and measuring an arterial blood pressure using the arterial line tube. In some variations, introducing the arterial line tube over the first wire into the femoral artery may further include subsequently removing the first wire from the femoral artery. In some variations, the first wire is bigger (e.g., 0.035") to introduce the first (operating), e.g., 6F, sheath. The second wire may be smaller (e.g., 0.018") and the arterial tube may be introduced over the second wire. The larger wire may be used to introduce the 6F sheath/dilator.

Many of the examples described and illustrated herein refer to femoral/groin approaches. It should be understood that these method and apparatuses (e.g., systems for performing them) may be used for any arterial approach, not limited to femoral, such as the brachial, radial, and carotid arteries. Further the sheathes described herein are referred to for convenience, as "groin sheaths"; these sheathes may be any appropriate sheath, not limited to those adapted for use in the groin or femoral region.

Measuring the arterial blood pressure may be performed continuously. Monitoring may begin as soon as the arterial line tube is introduced, continue during the surgical procedure, continue after the instrument has been removed from the second groin sheath, or any combination of these periods of time.

In some variations, removing the first groin sheath from the femoral artery after introducing the first wire and the second wire may include retaining the first wire disposed at a first position and the second wire disposed at a second position within the femoral artery. The first and second position may be the same position.

In some variations, performing the surgical procedure may include advancing at least one instrument through the second groin sheath into the femoral artery. In some embodiments, the method may further include removing the second groin sheath and the second wire from the femoral artery after completing the surgical procedure.

The method may further include removing the arterial line tube from the femoral artery. In some embodiments, removing the arterial line tube from the femoral artery may further include flushing the arterial line prior to removing the arterial line tube.

In some variations, the groin sheath may be configured to advance through the femoral artery and comprises a circumference less than a circumference of the femoral artery. In some variations, the groin sheath may include a groin sheath configured as a 4 French, 5 French, 6 French, 7 French, 8 French, and/or 9 French groin sheath. The groin sheath may include a proximal end, a tubing body and a distal end including an opening and a tapered region adjacent to the opening. The tapered region may have a circumference less than a circumference of the tubing body.

In some variations, the arterial line tube may be non-compressible. In some variations, the arterial line tube may be disposed adjacent the second groin sheath in the femoral artery.

In some variations, introducing the second groin sheath may include re-introducing the first groin sheath.

In another aspect, a method for monitoring an arterial blood pressure is provided, including: introducing a first groin sheath; introducing a first and a second wire into the first groin sheath into a femoral artery; removing the first groin sheath from the femoral artery; introducing a second groin sheath over the second wire into the femoral artery; introducing an arterial line tube over the first wire into the femoral artery; and measuring an arterial blood pressure using the arterial line tube. The first line may be removed before measuring pressure.

In some variations, introducing the second groin sheath or introducing the arterial line tube may further include subsequently advancing an instrument through the second groin sheath into the femoral artery. In some variations, the instrument may be a diagnostic instrument or a surgical instrument. The method may further include subsequently performing a diagnostic or surgical procedure within a blood vessel and/or organ accessible from the femoral artery.

In another aspect, a method for monitoring an arterial blood pressure is provided, including: introducing an arterial line tube into a femoral artery; disposing the arterial line tube adjacent to a groin sheath within the femoral artery; and measuring an arterial blood pressure using the arterial line tube. In some variations, introducing the arterial line tube may further include inserting the arterial line tube over a first wire disposed within the femoral artery. In some variations, the method may further include introducing at least one instrument through the groin sheath into the femoral artery.

In some variations, measuring the arterial blood pressure may be performed continuously. Measuring the arterial blood pressure in the arterial line tube adjacent to the groin sheath may reduce artifactual disruption.

In some variations, measuring the arterial blood pressure may be performed contemporaneously or subsequent to introducing the at least one instrument through the groin sheath and into the femoral artery. In some variations, measuring the arterial blood pressure in the arterial line tube adjacent to the groin sheath may be performed contemporaneously with moving the at least one instrument introduced into the groin sheath and femoral artery.

In some variations, the method may further include performing a diagnostic or therapeutic procedure.

In general, the methods and apparatuses (e.g., systems) described herein may include two separate sheaths, a first groin sheath that is used to place a pair of guidewires that may initially be positioned in tandem; this first sheath is then removed, and a second groin sheath is then applied over the first guidewire but with the second guidewire positioned outside of the second sheath and separate from it. The second groin sheath may be adapted to allow an instrument placed into the second groin sheath (and in some variations over the guidewire within the second groin sheath, to be operated independently and without interfering with an arterial line tube that is positioned outside of the second groin sheath using the guidewire outside of the second groin sheath (e.g., by sliding over the second groin sheath).

In any of these apparatuses and methods the second groin sheath may be adapted to ride alongside the external guidewire and/or an arterial line tube without disrupting the operation of the arterial line tube, including allowing continuous monitoring of pressure, even if or when one or more instruments are inserted into the second groin sheath and/or over the guidewire within the second groin sheath. For example, the outer surface of the second groin sheath may include an open channel or concavity configured to accommodate the external guide wire and/or arterial line tube. In some variations all or a portion of the second groin sheath may be lubricious.

The use of two (or more) sequentially applied groin sheaths as described herein may allow the arterial line tube to remain in place even after a first procedure is performed and the (e.g., work horse) groin sheath is removed. As mentioned, this prevents disruption of arterial monitoring as seen in other systems like the one above because as you introduce devices into the main sheath it will disrupt monitoring. The arterial line tube may be any appropriate size. In particular, the arterial line tube may be sufficiently small so that it can be pulled out of the groin with minimal manual pressure for hemeostasis versus a larger groin sheath.

For example, described herein are methods for monitoring arterial blood pressure (e.g., methods for monitoring a patient's arterial blood pressure), comprising: removing a first groin sheath from a femoral artery, wherein a first wire and a second wire are held within the first groin sheath and extend into the femoral artery; introducing a second groin sheath over the second wire and into the femoral artery so that the first wire is outside of the second groin sheath, wherein the second groin sheath may be a new groin sheath or may comprising the first groin sheath; introducing an arterial line tube over the first wire and into the femoral artery; performing a surgical procedure using the second groin sheath; and measuring an arterial blood pressure using the arterial line tube.

Any of these methods may include introducing the arterial line tube over the first wire into the femoral artery and subsequently removing the first wire from the femoral artery. The arterial blood pressure monitoring may be performed continuously.

In any of these methods, removing the first groin sheath from the femoral artery may include retaining the first wire disposed at a first position and the second wire disposed at a second position within the femoral artery.

The surgical procedure may include advancing at least one instrument through the second groin sheath into the femoral artery. The procedure may be any surgical and/or diagnostic procedure that may be performed through the vasculature with introduction from the groin sheath, including imaging and/or intervention, such as placement of stents and the like (e.g., angioplasty, balloon angioplasty, angiography, including coronary angiography and intervention and peripheral vascular angiography and intervention, valvuloplasty, balloon valvuloplasty, hemodynamic support, including intraortic balloon pump placement, hemodynamic monitoring, femoral endartectomy, neurointervention, coil embolization, embolic flow diversion, mechanical thrombectomy, thrombo-aspiration, etc.

Any of the methods described herein may include removing the second groin sheath and the second wire from the femoral artery after completing the surgical procedure. These methods may include continuing to measure the arterial blood pressure after completing the surgical procedure (e.g., for 10 minutes or more, 15 minutes or more, 20 minutes or more, 30 minutes or more, 45 minute or more 1 hour or more, 2 hours or more, 3 hours or more 4 hours or more, 6 hours or more, 7 hours or more, 10 hours or more, 12 hours or more 24 hours or more, 2 days or more, etc.).

In general, the second groin sheath may be adapted for inserting adjacent to the first or second wire. For example, introducing the second groin sheath over the second wire may include sliding the first wire within an open channel on an outer surface of the second groin sheath. In some variations introducing the second groin sheath may include sliding the second groin sheath over the second wire and sliding the second groin sheath against the first wire; in some variations the first wire may be within a channel on the second groin sheath, such as an open channel or guide. The proximal end of the second groin sheath may be adapted to form a funnel; the funnel-shaped end of the second groin sheath may be shaped to minimize interference with the first wire. For example, the funnel-shaped end may include a slot or opening through which the first wire may pass. The funnel-shaped end may include a flattened or invaginated region configured to pass the first wire on an outer surface of the second groin sheath. In general, the arterial line tube may be disposed adjacent the second groin sheath in the femoral artery.

In any of these methods, the first groin sheath may be introduced over the second wire; the first wire may be introduced into the femoral artery through the first groin sheath, prior to removing the first groin sheath.

The first groin sheath may be configured as a 6 French groin sheath. The second groin sheath may be as large (e.g., 6F) or smaller (e.g., 5F, 4F, 3F, etc.).

As mentioned, in some variations the second groin sheath may be the same as (and may reuse) the first groin sheath; thus inserting the second groin sheath may comprises re-introducing the first groin sheath. Alternatively, in some variations a different groin sheath may be used as the second groin sheath.

In general, the first wire and the second wire may be any thin, elongate flexible member that may be used for insertion into the vasculature to provide a guide for placement of another device, such as the groin sheath, arterial pressure line, instrument, etc. For example, the first wire may comprise a guidewire or a guide catheter and wherein the second wire comprises a guidewire or a guide catheter. The first and/or second wire may be sharp or blunt. In some variations the first wire has a diameter that is less than the second wire. For example, the first wire and/or the second wire may have a diameter of between about 0.01 and 0.04 inches (e.g., about 0.014, about 0.018, about 0.035 inches, etc.).

Any of these methods and apparatuses may include positioning the first groin sheath using the first and/or second wire. For example. A method for monitoring a patient's arterial blood pressure may include: introducing a first groin sheath into a femoral artery using a first wire; introducing a second wire into the femoral artery through the first groin sheath; removing the first groin sheath from the femoral artery leaving the first wire and the second wire extending into the femoral artery; introducing a second groin sheath over the first wire and into the femoral artery so that the second wire is outside of, and adjacent to, the second groin sheath; introducing an arterial line tube over the second wire and into the femoral artery; introducing and advancing an instrument through the second groin sheath into the femoral artery and performing a procedure within the patient using the instrument; and measuring arterial blood pressure using the arterial line tube during and after the procedure.

The instrument may be a diagnostic instrument or a surgical instrument. Thus, the procedure may be a diagnostic and/or surgical interventional procedure. In general, the procedure may be a procedure that is performed within an organ accessible from an artery, including (but not limited to) the femoral artery. Other arteries may include brachial, radial, and carotid.

As mentioned above, any of these methods may include measuring the arterial blood pressure continuously using the arterial line; this may be done before, during and/or after inserting an instrument and performing a procedure. Monitoring may be real-time monitoring. Monitoring may include displaying and/or recording arterial blood pressure. Continuous monitoring may include monitoring without interruption. Continuous may include determining arterial blood pressure at a sampling rate (of, e.g., x Hz, where x may 1 Hz or greater, 5 Hz or greater, 10 Hz or greater, 30 Hz or greater, 60 Hz or greater, 100 Hz or greater, 500 Hz or greater, 1000 Hz or greater, etc.); thus continuous monitoring may include uninterrupted, continuous sampling at the sampling rate. Arterial blood pressure measuring may be performed contemporaneously and subsequently to introducing the instrument, without significantly disrupting the blood pressure measurement, as described herein.

For example, a method for monitoring an arterial blood pressure may include: removing a first groin sheath from a femoral artery, wherein a first wire and a second wire are held within the first groin sheath and extend into the femoral artery; introducing a second groin sheath over the second wire and into the femoral artery so that the first wire is outside of the second groin sheath, wherein the second groin sheath may be a new groin sheath or may comprising the first groin sheath; introducing an arterial line tube over the first wire and into the femoral artery; introducing and advancing an instrument through the second groin sheath into the femoral artery; performing a procedure using the instrument; and continuously measuring an arterial blood pressure during and after the procedure using the arterial line tube.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 2, all of the dimensions shown are merely for illustration; other dimensions may be used.

DETAILED DESCRIPTION

Arterial blood pressure monitoring hemodynamically can offer superior understanding of moment-to-moment status of a subject and can be particularly useful when a diagnostic or therapeutic procedure may increase already unstable blood pressures observed in the patient, the procedure is designed to alter blood pressure, such as administration of vasoactive drugs or removing occlusions within the vasculature. Use of an arterial line also can be useful if frequent blood samples need to be taken prior, during or after a procedure is performed. A particularly useful type of arterial line insertion and monitoring is performed within the femoral artery, and permits a single access point for both arterial line blood pressure monitoring as well as any other instrumentation needed for a procedure.

However, the introduction and use of these other instruments can produce motion-related artifacts in the hemodynamic measurements being acquired at the same time, increasing noise and incorrect data. It is desirable to find new methods of introducing and insulating arterial line instrumentation and processes within the small circumference of femoral artery access points to improve the quality of blood pressuring monitoring results, for better diagnostic and therapeutic outcomes. Methods to isolate and insulate arterial line instrumentation can utilize complex cannulated devices with multiple lumen within the cannula. However, described herein are methods which do not rely upon such specialized structural devices to obtain superior isolation and insulation of femoral arterial lines for blood pressure monitoring, which may be continuous. Further, the arterial line may be left in place after the diagnostic/therapeutic procedure has been completed, to provide such continuous blood pressure monitoring during immediate and longer term recovery. In some variations, it may also be advantageous (e.g., may be less invasive) to accomplish multiple functions through a femoral access point.

Access to the femoral artery is highly useful for introduction and manipulation of surgical instruments, blood pressure arterial lines and other diagnostic instrumentation, which can include imaging devices. Often relied upon in order to assist with initiation of entry to the femoral artery and to introduce the above mentioned instruments and devices, groin sheaths may be used in the methods describe here, to not only assist with introduction of instruments and their manipulation or testing within the vasculature, but to also provide another capability, isolation and/or insulation from physical signals to reduce noise in the arterial line data and to render the hemodynamic results more robustly related to the actual, contemporaneous state of the subject.

The groin sheath may be any suitable groin sheath, but typically the groin sheath may have a size of about 4 French, about 5 French, about 6 French or in some instances, the size may be larger, e.g. up to about 10 French (e.g., 7 French, 8 French, 9 French, 10 French, etc.). The size of the groin sheath may be selected as appropriate to be capable of advancing through the femoral artery and comprises a circumference less than a circumference of the femoral artery.

The groin sheath may have a proximal end (closest to the operator), a tubing body and a distal end comprising an opening and a tapered region adjacent to the opening at the distal end. The tapered region may have a circumference less than a circumference of the tubing body, for ease of advancement within the femoral artery. The groin sheath may be made of a polymer, such as polypropylene, which may be stiff enough to permit advancement through the femoral artery without collapsing or kinking, but compliant enough to advance through the femoral artery without damaging arterial walls. In some variations, the groin sheath may include a hydrophilic coating to reduce biofouling and thrombus formation.

The groin sheath may be introduced in any suitable manner to the femoral artery; there are a variety of currently available protocols outlining appropriate siting, pre-testing and insertion techniques for the purview of one of skill to select appropriate conditions for introduction of a groin sheath. The puncture site may be selected to be at a location where the femoral artery is evident and close to the skin, e.g., may be made in or adjacent to the groin crease. The underlying support of the ligament running under the artery at that location, as well as the femoral bone, is helpful during removal procedures to provide compression points during removal.

A first and a second wire may be introduced into the groin sheath within a femoral artery. The first wire may be a wire having a size of about 0.018 in or less. In some variations, the first wire may be sized to fit within the cannula of an arterial line tube. The second wire may have a larger size, and may have a size of about 0.035 in or less. The first wire and second wire may be advanced through the groin sheath and each respective distal end may be advanced to a selected location in the femoral artery. In some variations, the location of the distal end of the first wire and the distal end of the second wire may be the same location within the femoral artery. The distal end of the first wire and/or a distal end of the second wire may be disposed about 5 cm, about 10 cm, about 15 cm, about 20 cm, or about 30 cm away from a respective proximal end of the first wire and/or the second wire. The distal end of the first wire and/or a distal end of the second wire may be disposed about 5 cm, about 10 cm, about 15 cm, about 20 cm, or about 30 cm away from the puncture site used to access the femoral artery.

After the first wire and the second wire are disposed within the femoral artery, the groin sheath may be removed from the femoral artery. The first wire and the second wire disposed at a second position may be retained within the femoral artery. The distal end of the first wire and/or a distal end of the second wire may not be disturbed significantly, and permits retention of the first wire and the second wire during the sheath removal process. The method may further comprise flushing the groin sheath before its removal, to prevent thrombus formation.

For example, the two wires may be held in place with manual pressure. In some variations the first wire may be, e.g., a 0.018 inch wire for the introduction of the hemodynamic monitoring device. The arterial sheath may be placed over the second wire, such as a 0.035 inch wire. The hemodynamic monitoring device may be introduced over the first inch wire and the arterial sheath may be introduced over the second wire, and both wires can then be removed, leaving an arterial sheath which can be used to increase catheters and devices to treat the patient and the hemodynamic monitoring device adjacent to it.

A second groin sheath may then be introduced, passing over the second wire, into the femoral artery. The second groin sheath may be a new groin sheath having any of the characteristics of the first groin sheath, or it may be the same groin sheath, just reintroduced. However, during this introduction, the second groin sheath does not include the first, thinner wire. The first (and thinner) wire has remained in place throughout the introduction/re-introduction of the groin sheath passing over only the second wire. At the end of the introduction, the first wire is disposed alongside or adjacent to the second or reinstalled groin sheath. The first wire is no longer adjacent to the second wire, as the second/reinstalled groin sheath is interposed, and insulates the first wire from any motion that the second wire may make.

An arterial line tube for monitoring blood pressure characteristics is then introduced, by passing the arterial line tube over the first wire into the femoral artery, using the first wire as a guide for entry. The arterial line tube may be a non-compressible tube. Any suitable arterial line tube may be used and it may further include additional control side arms, compressible tubing for the external pressure loop, and a transducer.

In some variations, after the arterial line tube is introduced into the femoral artery, over the first wire, the first wire may be removed from the femoral artery. This may be performed by withdrawing the first wire at the proximal end, outside of the femoral artery.

After the arterial line tube has been introduced, other diagnostic or therapeutic instrumentation may be introduced through the groin sheath into the femoral artery. This introduction may be prefaced by flushing the groin sheath. Any suitable kind of diagnostic or therapeutic intervention may be performed. In some variations, it is a surgical procedure such as ablation therapies, and the like. In other variations, the therapeutic intervention may include physical, chemical or electrical disruption of physical occlusions or electrical interventions for arrhythmia. In other variations, a diagnostic procedure may be performed. One or more instruments may be introduced into the groin sheath and may use the second wire as a guide wire. In some variations, the second wire is removed from the femoral artery upon introduction of the one or more instruments.

After the diagnostic/therapeutic intervention is completed, any of the instruments introduced via the second groin sheath may be removed from the femoral artery and second groin sheath, by withdrawing from the proximal end of the instrument external to the femoral artery. Subsequently, the second groin sheath may also be withdrawn from the femoral artery.

As mentioned above, once the arterial line tube has been introduced, any kind of blood pressure measurement may be performed, using the arterial line tube. In some variations, the monitoring may be continuous. The monitoring may begin as soon as the arterial line tube is introduced, and optionally, the first wire removed. The monitoring may continue during the diagnostic/therapeutic intervention, may continue after any diagnostic/therapeutic instruments are removed after the end of the intervention. Monitoring may continue after the intervention has been completed for any suitable amount of time.

Besides blood pressure data itself, the arterial line may be used to obtain pulse rate and rhythm, effects of dysrhythmia on perfusion, detection of ECG lead disconnection, monitoring of continuous cardiac output using pulse contour analysis, where specific wave form morphologies might be diagnostic of problems such as tamponade, detection of pulse pressure variation (suggesting fluid responsiveness), and observation of steeper upstroke of pulse pressure, indicating increased contractility. This is a non-limiting list, and one of skill may determine other blood pressure characteristics using the methods described herein.

After the diagnostic/therapeutic intervention has been completed, and after any extended monitoring has been completed, the arterial line tube may then be removed from the femoral artery. In some variations, removing the arterial line tube from the femoral artery may further include flushing the arterial line prior to removing the arterial line tube.

In some other variations, a method for monitoring an arterial blood pressure may include introducing a first groin sheath, which may be like any groin sheath described herein. A first and a second wire is introduced into the first groin sheath into a femoral artery, which may be like the first and second wires described herein. After introduction of the first and the second wires, the first groin sheath may be removed from the femoral artery. Subsequently a second groin sheath is introduced over the second wire into the femoral artery. The first wire is excluded from the lumen of the second groin sheath and is therefore insulated or isolated from any instrumentation within the lumen of the second groin sheath. An arterial line tube is introduced over the first wire into the femoral artery; and an arterial blood pressure is measured using the arterial line tube. In some variations, introducing the second groin sheath or introducing the arterial line tube further includes subsequently advancing an instrument through the second groin sheath into the femoral artery. The instrument may be a diagnostic instrument or a surgical instrument. In some variations, a diagnostic or surgical procedure may be performed within a blood vessel and/or organ accessible from the femoral artery.

In another variation, a method for monitoring an arterial blood pressure, may include introducing an arterial line tube into a femoral artery; disposing the arterial line tube adjacent to a groin sheath within the femoral artery; and measuring an arterial blood pressure using the arterial line tube. In some variations, introducing the arterial line tube may further include inserting the arterial line tube over a first wire disposed within the femoral artery. The first wire may be disposed adjacent or parallel to or alongside the groin sheath. In some variations, the method further includes introducing at least one instrument through the groin sheath into the femoral artery.

In some variations, measuring the arterial blood pressure may be performed continuously. Measuring the arterial blood pressure in the arterial line tube adjacent to the groin sheath may reduce artifactual disruption of blood pressure characteristics. Measuring the arterial blood pressure may be performed contemporaneously or subsequent to introducing the at least one instrument through the groin sheath and into the femoral artery. In some variations, measuring the arterial blood pressure in the arterial line tube adjacent to the groin sheath may be performed contemporaneously with moving the at least one instrument introduced into the groin sheath and femoral artery.

In some variations, the method may include performing a diagnostic or therapeutic procedure.

Example. Method of Monitoring Arterial Blood Pressure

Figure 1A:
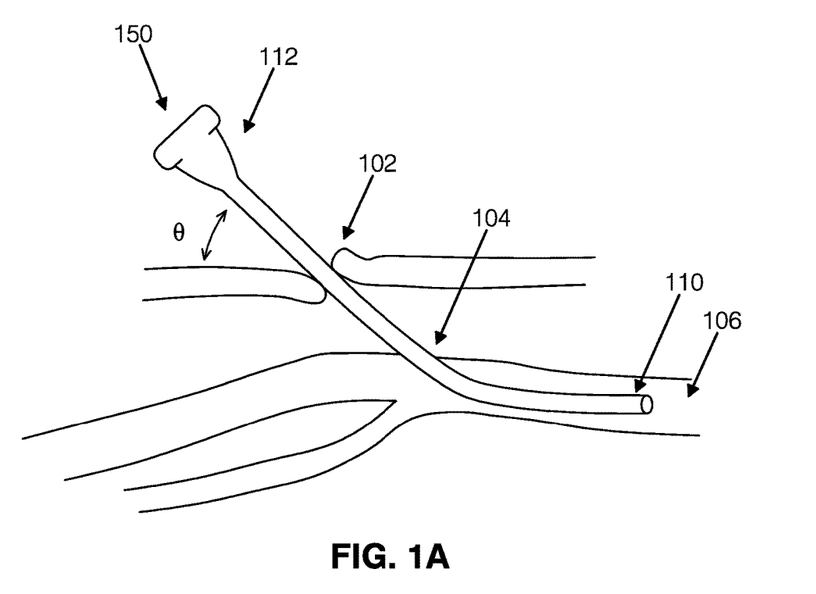
FIGS. 1A to 1D are graphical representations of a method for arterial blood pressure monitoring according some embodiments of the disclosure.

A groin sheath is introduced into a femoral artery by first puncturing the skin at a region within the groin crease on the right side of the subject, at a location where the femoral artery is located close to the skin and/or over underlying supporting bone and ligament structures, e.g., where the inguinal ligament passes under the common femoral artery. The puncture at site 102 also enters the femoral artery itself at site 104, and is performed at an angle θ of about 30° relative to the surface of the skin of the subject to minimize dual wall puncture of the artery. Additional visualization aids may be employed to assist with the insertion and advancement of the groin sheath, such as ultrasound or fluoroscopic imaging. The groin sheath is a size 6 French sheath, which is sized to fit within the femoral artery of most patients without excessive risk of excessive puncture as the groin sheath is advanced along the artery. As shown in FIG. 1A, distal end 110 of the groin sheath is advanced with care within the femoral artery 106 to about 5 cm to 10 cm within the artery. The proximal end 112 of the groin sheath 150 is retained outside of the incision.

Figure 1B:
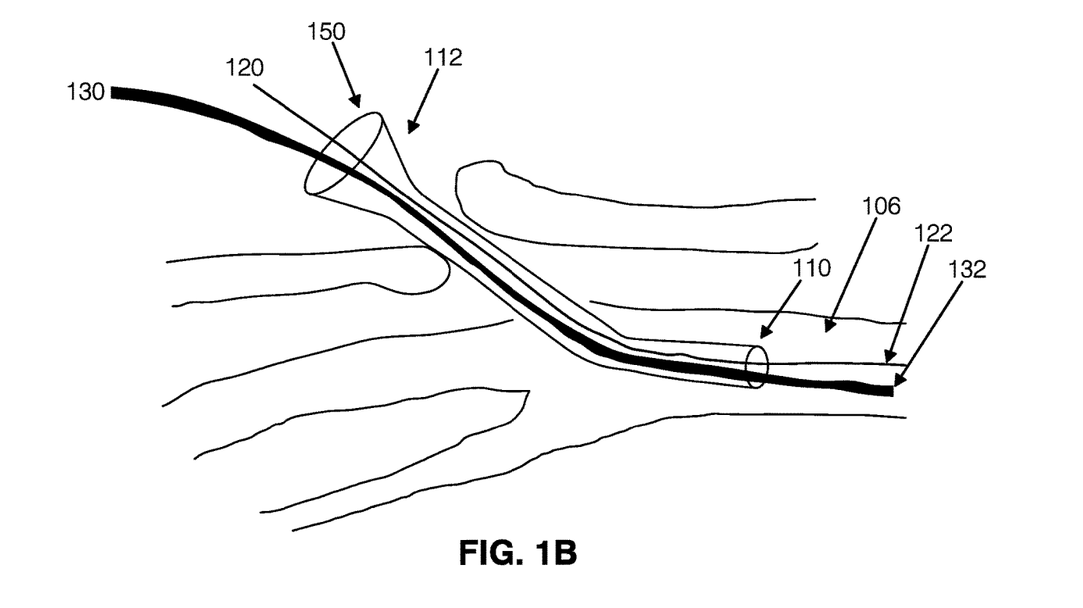

After groin sheath 150 placement is complete, wires 120 and 130 are inserted into the proximal end 112 of groin sheath 150, and both wires 120, 130 are advanced through the distal end 110 of the groin sheath and carefully advanced further into the femoral artery to place each of the distal end 122, of wire 120, and distal end 132 of wire 130 a total distance of about 15 cm, as shown in FIG. 1B. Wire 120 is selected to be a 0.018 inch wire and wire 130 is a 0.035 inch wire, and can be manipulated within the inner diameter of the groin sheath 150.

Figure 1C:
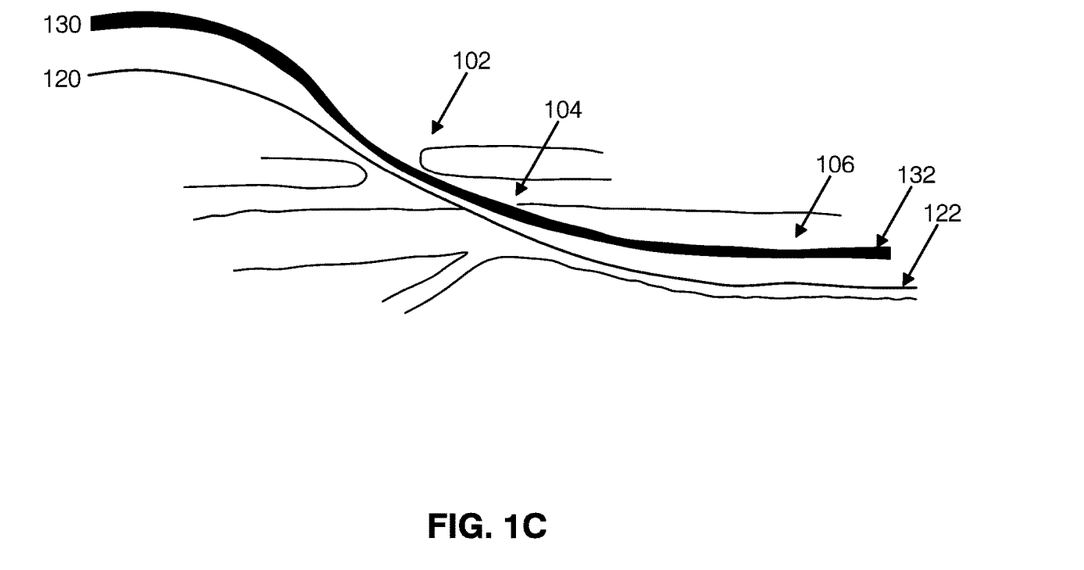

The groin sheath 150 is then removed from the femoral artery, to prepare the monitoring/instrumentation entry site for introduction of the monitoring instrumentation, and in some variations, for introduction of one or more instruments into the femoral artery. As shown in FIG. 1C, the sheath 150 has been removed, but wires 120, 130 have been left in place within the femoral artery, entering the femoral artery at site 104 and with the distal end 122 of wire 120 and the distal end 132 of wire 130 at the location to which each had been advanced.

Following excision of the groin sheath 150 which has encompassed both wire 120 and 130, a new (or in some variations, the same) groin sheath 150' is introduced, using the thicker wire 130 as a guide wire to advance the groin sheath 150' in through the incision site 102, and arterial puncture site 104, to advance part way along the length of guide wire 130. However, this introduction does not include wire 120 within the lumen of groin sheath 150'. In contrast, groin sheath 150' is introduced adjacent to wire 120, encompassing only wire 130. The newly installed (or reinstalled) groin sheath 150' acts as a barrier between wires 120 and 130.

Figure 1D:
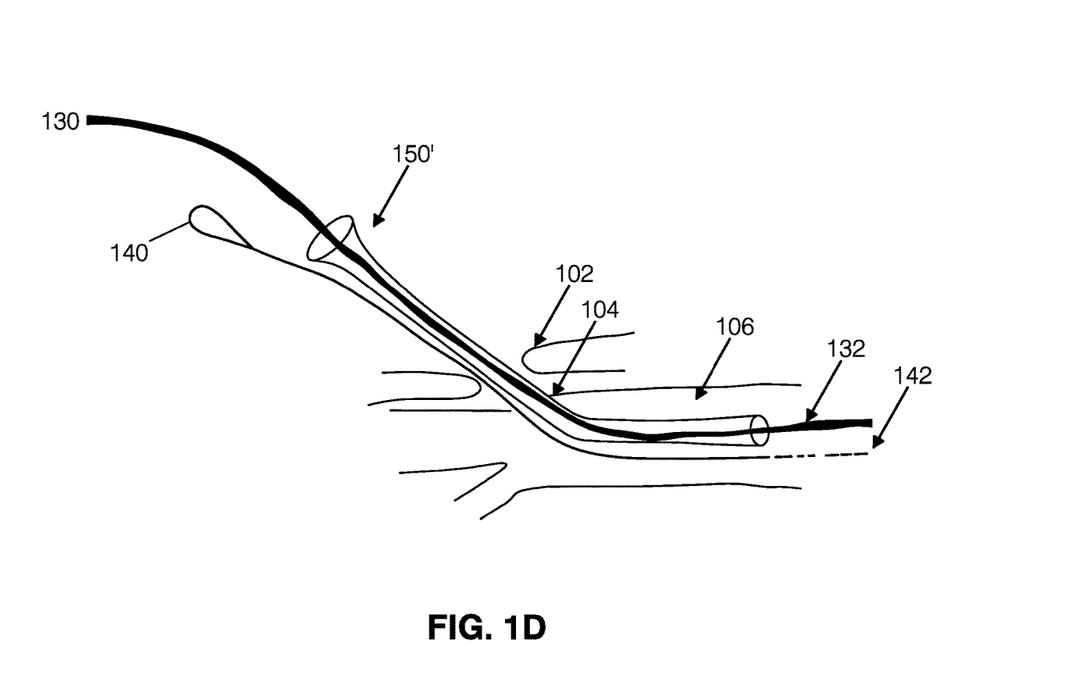

As shown in FIG. 1D, an arterial line tube 140 is now introduced, using wire 120 as a guide wire. Arterial tube 140 is introduced by passing wire 120 through the central opening of arterial tube 140, and advancing the distal end 142 of the arterial tube 140 to a distance about 15 cm within the femoral artery from the incision sites 102/104. In this instance, wire 120 is removed from within the femoral artery and leaves the central channel of the tube free for flushing and for arterial blood pressure measurements. Blood pressure measurements may be performed in any way desired, once this instrumentation has been introduced.

Not shown here, but included within the method, wire 130 is used either as a guide wire or is removed to permit instrumentation for diagnostics or therapeutic interventions to be introduced and advanced to the site of diagnostics/intervention within the femoral artery.

After the desired diagnostic or therapeutic intervention, is complete, the diagnostic/therapeutic instrumentation is withdrawn from the femoral artery, and wire 130, if still retained within the groin sheath 150' is then removed as well.

During the processes of introduction of instrumentation and any guide wires needed, and further manipulation required to get diagnostic/therapeutic instrumentation to the desired remote site, the presence of the groin sheath 150' adjacent to the arterial line tube 140, insulates and isolates arterial line tube 140 from displacements caused by manipulation of the wires/instruments being passed through or adjusted within the groin sheath 150', reducing noise in the blood pressure data being monitored. Once the instrumentation/wire 130/groin sheath 150' have been removed at the end of the diagnostic/therapeutic intervention, the arterial line tube 140 may be retained in place to continue monitoring the subject for a desired period of time, post-intervention.

Figure 2:
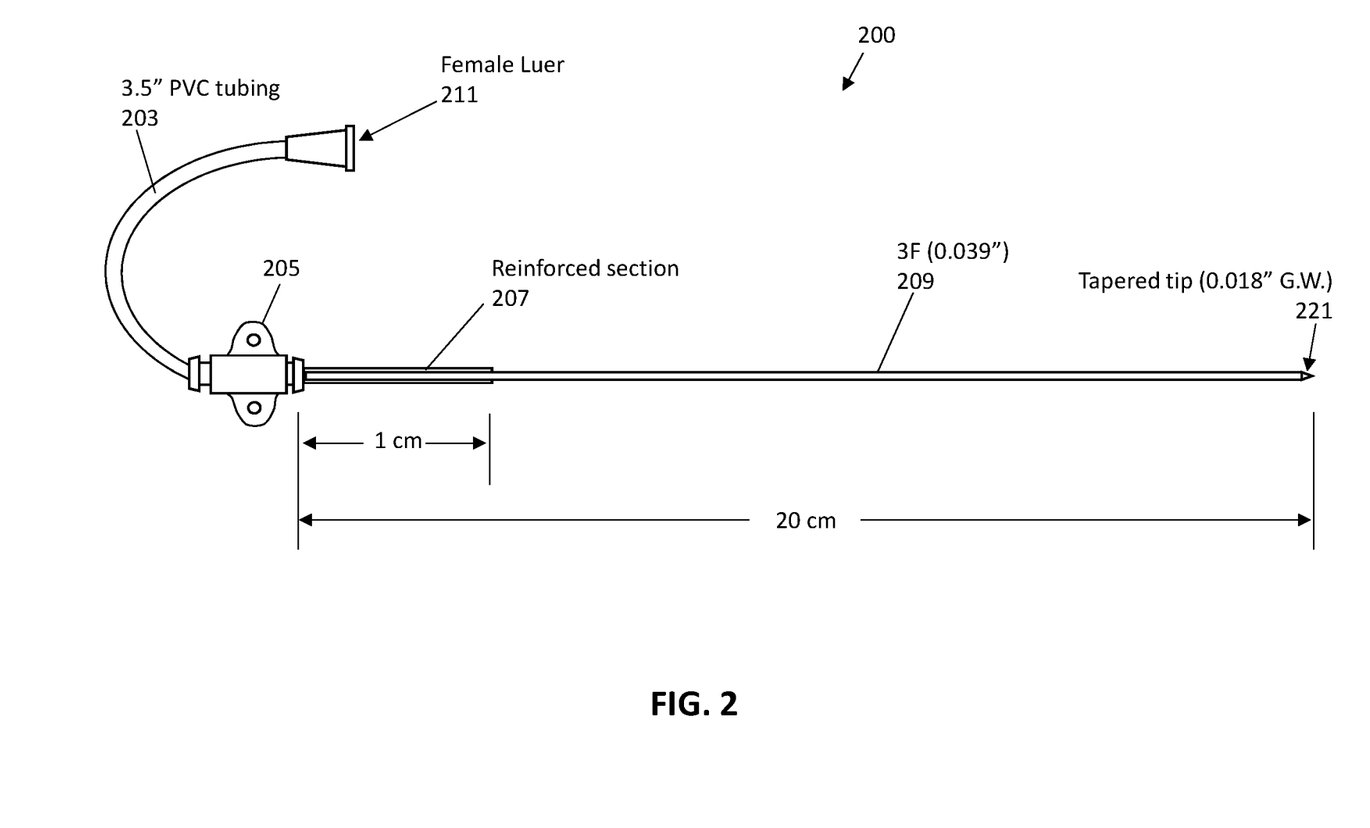
FIG. 2 illustrates one example of an arterial line tube that may be used to measure arterial blood pressure as described herein.

In general, the arterial lines (arterial line tubes) described herein may be positioned over a guidewire and used adjacent to a groin sheath, as described above. Any appropriate arterial line may be used. In general, an arterial line (a-line or art-line) may include a thin catheter and may be adapted for measuring blood pressure directly and in real time and/or to obtain samples of blood for arterial blood gas analysis or for otherwise sampling blood. FIG. 2 illustrates one example of an arterial line that may be used in the methods described herein. In FIG. 2, the arterial line 200 includes a catheter region 209 having a tapered tip 221 that can be inserted over a guidewire and into the body. The device may also include a reinforced proximal region 207 and an anchoring region 205. The device may also include one or more flexible tubes coupled to a lure (e.g., female luer 211) to be coupled to, e.g., a pressure sensor, etc.

In this example the device has a catheter that is approximately 20 cm long, with a 1 cm reinforced proximal region. The catheter is approximately 3F, although other sizes could be used. In general, the dimensions illustrated in FIG. 2 represent a single example; other sizes may be used. For example, in some variations the sizes may be +/−5%, 10%, 15%, 20%, 25%, 30%, 35%, 40%, 50%, 60%, 75%, 100%, or more in one or more of the dimensions illustrated. Thus, the cannula region 209 may be longer or shorter than illustrated, and/or may have a larger or smaller inner and/or outer diameter. Suture tabs can be provided for securement during monitoring.

Figure 3:
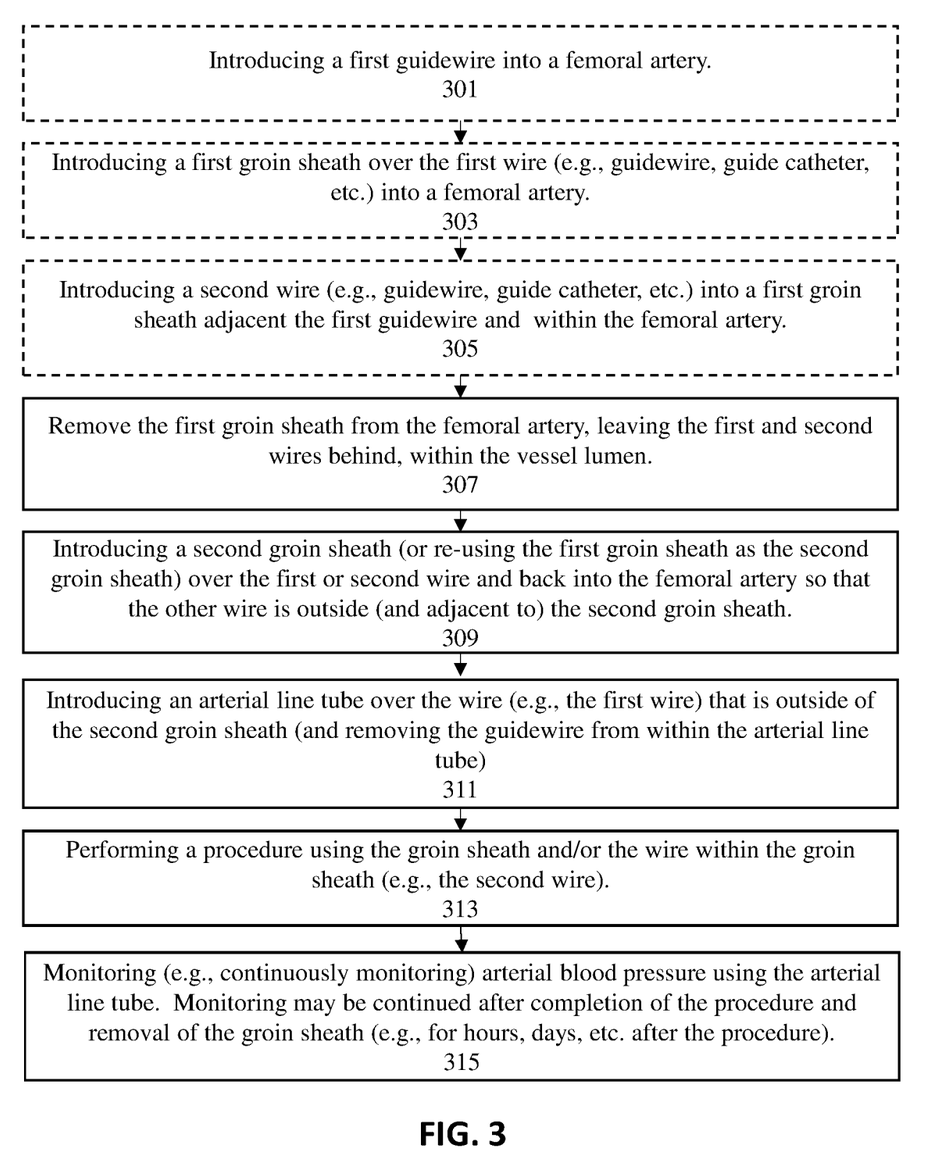
FIG. 3 schematically illustrates one example of a method of monitoring arterial blood pressure, as described herein.

When used as described herein, the desired vessel or cavity (e.g., the femoral artery) may be punctured with a sharp hollow needle, with ultrasound guidance if necessary. A round-tipped guidewire may then be advanced through the lumen of the needle, and the needle may be withdrawn. Thus a first (or in some cases first and second) guidewire may be introduced into a femoral artery 301. In any of these variations a dilator may be used, e.g., for introducing one or more components. A sheath (e.g., first groin sheath) or blunt cannula can now be passed over the first guidewire into the cavity or vessel 303. In some variations the sheath may be introduced using a dilator (e.g., a dilator having a tapered tip); for example, a dilator may take up the space between the wire diameter and the sheath inner diameter. A second guidewire, having different or the same dimensions, may then be placed into the vessel through the first groin sheath 305. The first groin sheath may then be removed 307. The same or a different groin sheath (e.g., a second groin sheath) may then be positioned over the first (or second) guidewire, while the other guidewire (the second or first guidewire) is excluded from the lumen of the second groin sheath 309. As mentioned, the second groin sheath may be the same sheath or a similar sheath as the first groin sheath; alternatively the second groin sheath may be a new, second groin sheath. Alternatively, in some variations the guidewires may both be positioned together within the vessel lumen without using a first groin sheath. An arterial line tube may then be introduced over the guidewire that is outside of the groin sheath 311.

In some variations at least the second groin sheath may be adapted for use in tandem with the arterial line tube (or a guidewire used to position the arterial line tube) on the outside and adjacent to the sheath. For example, in variations in which an open channel is formed on the outside of the (second) groin sheath, the arterial line tube may be slid against the outside surface of the second groin sheath during positioning of the arterial line. In any of these variations the arterial line tube may slide within an external open channel in the second groin sheath. In any of these variations the arterial line tube may slide against a lubricious surface (or in some variations, a channel, including an open channel) on the outer surface of the second groin sheath.

FIG. 3 illustrates one example of a method of measuring arterial blood pressure as described herein. In FIG. 3, once the arterial line tube is positioned outside of the groin sheath and separate from the guidewire within the groin sheath, the external guidewire may be removed and the arterial line tube may be used for continually monitoring arterial blood pressure or other uses (e.g., blood sampling) 313. Concurrently, one or more procedures may be performed through the groin sheath and/or using the guidewire within the groin sheath, allowing access within the femoral artery.

As described above, the first and second wires (guidewires) maybe different sizes. In some variations the first groin sheath may be introduced initially using a needle to position the first guidewire (e.g., a blunt-tipped or soft-tipped, e.g. a soft J tip guidewire) into the vessel lumen, then positioning the first groin sheath over the first guidewire. The second guidewire may then be positioned adjacent to the first guidewire down the first groin sheath.

In some variations, the first groin sheath may be removed from the vessel (e.g., the femoral artery), leaving the first and second guidewires in position. Thereafter, the same or a different groin sheath (in either case, referred to therein as a second groin sheath; note that the second groin sheath may be the same groin sheath as the first groin sheath, or it may be a new groin sheath).

In general, a groin sheath (which may also be referred to herein as a femoral sheath), may be any funnel-shaped sheath that enhances or improves the insertion of a device (including a guidewire or other vascular device) into a blood vessel or lumen within the body. A second groin sheath may then be introduced into the vessel over the second wire into the femoral artery. Thus, the second guidewire, which may be a different size (e.g., length, gauge/diameter, roughness, etc.) or may otherwise be distinguishable from the first guidewire may be positioned adjacent to the first guidewire.

In any of these methods and apparatuses, fluoroscopy may be used to confirm the position of the guidewire(s), sheaths and/or devices within the vessel lumen and/or to maneuver it to the desired location. Injection of radiocontrast may be used to visualize. Any procedure (e.g., step 313, above) may be performed, including, for example, interventional procedures, such as thermoablation, angioplasty, embolization or biopsy. Typically, upon completion of the desired procedure, the sheath is withdrawn. As mentioned, the arterial line tube may be left in place for hours or even days, to allow continued monitoring.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for monitoring an arterial blood pressure, comprising:
    removing a first groin sheath from a femoral artery, wherein a first wire and a second wire are held within the first groin sheath and extend into the femoral artery;
    introducing a second groin sheath over the second wire and into the femoral artery so that the first wire is outside of the second groin sheath, wherein the second groin sheath may be a new groin sheath or may comprising the first groin sheath;
    introducing an arterial line tube over the first wire and into the femoral artery;
    performing a surgical procedure using the second groin sheath; and
    measuring an arterial blood pressure using the arterial line tube.

2. The method of claim 1, wherein introducing the arterial line tube over the first wire into the femoral artery further comprises subsequently removing the first wire from the femoral artery.

3. The method of claim 1, wherein measuring the arterial blood pressure is performed continuously.

4. The method of claim 1, wherein removing the first groin sheath from the femoral artery comprises retaining the first wire disposed at a first position and the second wire disposed at a second position within the femoral artery.

5. The method of claim 1, wherein performing the surgical procedure comprises advancing at least one instrument through the second groin sheath into the femoral artery.

6. The method of claim 1, further comprising removing the second groin sheath and the second wire from the femoral artery after completing the surgical procedure.

7. The method of claim 1, further comprising continuing to measure the arterial blood pressure after completing the surgical procedure.

8. The method of claim 1, further comprising wherein introducing the second groin sheath over the second wire comprises sliding the first wire within an open channel on an outer surface of the second groin sheath.

9. The method of claim 1, further comprising introducing the first groin sheath over the second wire and introducing the first wire into the femoral artery through the first groin sheath, prior to removing the first groin sheath.

10. The method of claim 1, wherein the first groin sheath comprises a 6 French groin sheath.

11. The method of claim 1, wherein the arterial line tube is disposed adjacent the second groin sheath in the femoral artery.

12. The method of claim 1, wherein introducing the second groin sheath further comprises re-introducing the first groin sheath.

13. The method of claim 1 wherein the first wire comprises a guidewire or a guide catheter and wherein the second wire comprises a guidewire or a guide catheter.

14. The method of claim 1, wherein the first wire has a diameter that is less than the second wire.

15. A method for monitoring a patient's arterial blood pressure, comprising:
    introducing a first groin sheath into a femoral artery using a first wire;
    introducing a second wire into the femoral artery through the first groin sheath;
    removing the first groin sheath from the femoral artery leaving the first wire and the second wire extending into the femoral artery;
    introducing a second groin sheath over the first wire and into the femoral artery so that the second wire is outside of, and adjacent to, the second groin sheath;
    introducing an arterial line tube over the second wire and into the femoral artery;
    introducing and advancing an instrument through the second groin sheath into the femoral artery and performing a procedure within the patient using the instrument; and
    measuring arterial blood pressure using the arterial line tube during and after the procedure.

16. The method of claim 15, wherein the instrument is a diagnostic instrument or a surgical instrument.

17. The method of claim 15, wherein the procedure is performed within an organ accessible from the femoral artery.

18. The method of claim 15, wherein measuring the arterial blood pressure is performed continuously.

19. The method of claim 15, when measuring the arterial blood pressure is performed contemporaneously and subsequently to introducing the instrument.

20. A method for monitoring an arterial blood pressure, comprising:

removing a first groin sheath from a femoral artery, wherein a first wire and a second wire are held within the first groin sheath and extend into the femoral artery;

introducing a second groin sheath over the second wire and into the femoral artery so that the first wire is outside of the second groin sheath, wherein the second groin sheath may be a new groin sheath or may comprising the first groin sheath;

introducing an arterial line tube over the first wire and into the femoral artery;

introducing and advancing an instrument through the second groin sheath into the femoral artery;

performing a procedure using the instrument; and continuously measuring an arterial blood pressure during and after the procedure using the arterial line tube.

* * * * *